US012322298B2

(12) United States Patent
Alterman et al.

(10) Patent No.: US 12,322,298 B2
(45) Date of Patent: Jun. 3, 2025

(54) PROSTHESIS SIMULATOR DEVICES AND METHODS

(71) Applicant: Georgia Tech Research Corporation, Atlanta, GA (US)

(72) Inventors: Bennett Leonard Alterman, Atlanta, GA (US); William D. Hendrix, Lexington, KY (US); John T. Johnson, Atlanta, GA (US); Perry J. Lee, Marietta, GA (US); Lewis A. Wheaton, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 18/385,169

(22) Filed: Oct. 30, 2023

(65) Prior Publication Data

US 2024/0062681 A1 Feb. 22, 2024

Related U.S. Application Data

(63) Continuation of application No. 17/469,730, filed on Sep. 8, 2021, now Pat. No. 11,869,380.

(60) Provisional application No. 63/075,540, filed on Sep. 8, 2020.

(51) Int. Cl.
*G09B 23/32* (2006.01)
*A61F 2/58* (2006.01)
*A61F 2/68* (2006.01)
*A61F 5/37* (2006.01)

(52) U.S. Cl.
CPC .............. *G09B 23/32* (2013.01); *A61F 2/586* (2013.01); *A61F 2/68* (2013.01); *A61F 5/3723* (2013.01)

(58) Field of Classification Search
CPC .......... A61F 2/583; A61F 2/586; A61F 2/588; A61F 5/05866; A61F 5/0118; A61F 5/3723; A61F 4/00; A61F 2002/502; G09B 23/32
See application file for complete search history.

(56) References Cited

U.S. PATENT DOCUMENTS

| 1,211,423 | A | 1/1917 | Eisen |
| 10,561,507 | B1 | 2/2020 | Asada |
| 2003/0114783 | A1 | 6/2003 | Vanden |

(Continued)

FOREIGN PATENT DOCUMENTS

WO 2019013457 A1 1/2019

OTHER PUBLICATIONS

Bloomer, "Creating a Standardized, Quantitative Training Protocol for Upper Limb Bypass Prostheses," Physical Medicine and Rehabilitation Research (2018).

(Continued)

*Primary Examiner* — Christie Bahena
(74) *Attorney, Agent, or Firm* — Troutman Pepper Locke LLP; Ryan A. Schneider; Andrew C. Doherty

(57) ABSTRACT

Prosthesis simulator devices including a first restraint configured to restrain one or more fingers of a wearer of the simulator, a second restraint configured to restrain a thumb of the wearer, and a plurality of artificial digits configured to move in a manner to simulate one or more prosthetic fingers and a prosthetic thumb of a prosthesis. The first restraint can be attached to a roof plate connected to a base plate and defining a dorsal side of the prosthesis simulator. The second restraint can be attached to a holster connected to the base plate on a palmar side of the prosthesis simulator. Also disclosed herein are methods of using the same.

20 Claims, 15 Drawing Sheets

(56) References Cited

U.S. PATENT DOCUMENTS

2005/0101898 A1    5/2005   Cohen
2017/0056208 A1    3/2017   Thompson et al.
2018/0098862 A1    4/2018   Kuiken et al.

OTHER PUBLICATIONS

Huinink, "Learning to Use a Body-Powered Prosthesis: Changes in Functionality and Kinematics," Journal of Neuroengineering and Rehabilitation.
Blustein, "Assessing the Quality of Supplementary Snesory Feedback Using the Crossmodal Congruency Task," Scientific Reports (2018).
IEEE A Modular Transradial Bypass Prosthesis for Surface Myoelectric Control in Non-Amputees, IEEE.org (2019).
Wilson, "A Third Arm—Design of a Bypass Prosthesis Enabling Incorporation," Researchgate 2017.
Loughrin, "3D-Printed Arm Produced at Low Cost," 2017.
Wiki Pheonix Hand Oct. 2019.
TRS 1. TRS Prsthetic Simulator screen shots, Youtube 2017.
TRS 2. TRS Prosthetic Simulator screen shots. Youtube 2017.

PROSTHESIS SIMULATOR DEVICES AND METHODS

CROSS-REFERENCE TO RELATED APPLICATIONS

This is a continuation application of U.S. application Ser. No. 17/469,730 filed 8 Sep. 2021, which application claims the benefit of U.S. Provisional Application Ser. No. 63/075,540 filed 8 Sep. 2020, the entire contents and substance of which are incorporated herein by reference in their entirety as if fully set forth below.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

SEQUENCE LISTING

Not Applicable

STATEMENT REGARDING PRIOR DISCLOSURES BY THE INVENTOR OR A

Not Applicable

BACKGROUND OF THE DISCLOSURE

1. Field of the Invention

The present disclosure relates generally to prosthesis simulator devices and methods. Particularly, embodiments of the present disclosure relate to prosthesis simulator devices, amputation simulator devices, and methods of using the same.

2. Description of Related Art

It is projected that by this year, there will be 2.2 million persons with limb loss in the United States. Trauma accounts for most upper limb amputations, most commonly recreational or workplace accidents. The two most common levels of upper limb amputation are partial hand and trans radial. For workplace related amputations, the US Bureau of Labor Statistics reports that between 2011 and 2016 there were 33,000 amputations of which 31,740 involved the upper limb. In 2016, amputation had a low prevalence but had the fourth highest impact in median days from work of all musculoskeletal injuries. Of the 31,740 upper limb amputations, nearly half involved absence from work exceeding 31 days. The majority do not return to the workforce.

For amputees, artificial limbs (or prostheses) could become a vital part of their lives. Unfortunately, approximately 33% of upper limb amputees reject prostheses, and among those who opt for prostheses, approximately 75% of users use their devices as a non-functional aesthetic. Rehabilitation during the acute stages is largely aimed at developing compensatory strategies, which can impede functional outcomes of prostheses. There is urgency for upper extremity amputees to regain normalcy with their devices, because "successful" functional and psychosocial adaptation can play a significant role in positively affecting self-worth and self-efficacy. Predominant prosthesis options for amputees are body powered devices that use a cable system actuated by a joint movement, or myoelectric devices that are powered by muscle. Myoelectric devices come with a significant expense, may not be appropriate for all amputees, and are oftentimes beyond the range of healthcare reimbursement. One of the critical problems with prostheses is that it is difficult to understand the motor control problems that amputees have with prostheses and how these problems impact prosthesis use.

What is needed, therefore, are prosthesis simulator devices and methods to increase prosthesis use and training abilities. Embodiments of the present disclosure address this need as well as other needs that will become apparent upon reading the description below in conjunction with the drawings.

SUMMARY OF THE DISCLOSURE

The present disclosure relates generally to prosthesis simulator devices and methods. Particularly, embodiments of the present disclosure relate to prosthesis simulator devices, amputation simulator devices, and methods of using the same.

An exemplary embodiment of the present disclosure can provide a prosthesis simulator comprising a first restraint configured to restrain one or more fingers of a wearer of the simulator, a second restraint configured to restrain a thumb of the wearer, and a plurality of artificial digits configured to move in a manner to simulate one or more prosthetic fingers and a prosthetic thumb of a prosthesis.

In any of the embodiments disclosed herein, the prosthesis simulator can further comprise a cuff on a proximal end of the prosthesis simulator, the cuff configured to detachably attach to an arm of the wearer, a base plate hingedly coupled to the cuff thereby allowing the base plate to rotate relative to the cuff, and a rod connecting the plurality of artificial digits to the base plate, wherein an articulation of the base plate relative to the cuff causes an articulation of the plurality of artificial digits by the rod.

In any of the embodiments disclosed herein, the first restraint can be attached to a roof plate connected to the base plate and defining a dorsal side of the prosthesis simulator and the second restraint can be attached to a holster connected to the base plate on a palmar side of the prosthesis simulator.

In any of the embodiments disclosed herein, the first restraint can be slidably attached to the roof plate such that the first restraint can be positioned at varying distances away from the base plate.

In any of the embodiments disclosed herein, the prosthesis simulator can further comprise a joint connecting the base plate to the cuff, wherein the rod attaches thereto.

In any of the embodiments disclosed herein, the plurality of artificial digits can be positioned in a 3 jaw chuck grasp.

In any of the embodiments disclosed herein, each of the plurality of artificial digits can comprise a polymer material and a silicone-based material.

In any of the embodiments disclosed herein, the prosthesis simulator can further comprise a base plate, a roof plate connected to the base plate and defining a dorsal side of the prosthesis simulator, and a holster connected to the base plate on a palmar side of the prosthesis simulator opposite the dorsal side, wherein the one or more artificial digits extend from the base plate on the palmar side of the prosthesis simulator, wherein the first restraint is configured to restrain the one or more fingers of an unaffected hand of the wearer of the prosthesis simulator to the roof plate, wherein the second restraint is configured to restrain the thumb of the unaffected hand of the wearer, wherein the second restraint is attached to the holster, and wherein the one or more artificial digits are configured to move in a manner to simulate the one or more prosthetic fingers and the prosthetic thumb of the prosthesis worn on an affected hand of the wearer.

In any of the embodiments disclosed herein, the prosthesis simulator can further comprise a cuff on a proximal end of the prosthesis simulator, the cuff configured to detachably attach to the arm with the unaffected hand of the wearer, a joint connecting the base plate to the cuff, and a rod connecting the artificial digits to the base plate, wherein an articulation of the base plate relative to the cuff causes an articulation of the artificial digits by the rod.

In any of the embodiments disclosed herein, the prosthesis simulator can be further configured to preserve the wearer's perception of arm length of the arm with the unaffected hand.

In any of the embodiments disclosed herein, the first restraint and the second restraint can be further configured to restrain portions of the unaffected hand in an open hand posture.

In any of the embodiments disclosed herein, the first restraint can be further configured to be slidably attached to the roof plate such that the first restraint can be positioned at varying distances away from the base plate.

In any of the embodiments disclosed herein, the one or more artificial digits can form at least a portion of a 3 jaw chuck grasp with the thumb constrained at a right angle secured along the palm of the unaffected hand.

In any of the embodiments disclosed herein, the prosthesis simulator can be further configured to enable the wearer to perform a task with at least one of the artificial digits via the articulation of the base plate relative to the cuff, causing the articulation of the artificial digits by the rod.

In any of the embodiments disclosed herein, the prosthesis simulator can be a partial-hand prosthesis simulator (PhPS), wherein the task comprises wrist flexion and closing through wrist extension, and wherein each artificial digit comprises a polymer material.

Another example embodiment of the present disclosure can provide a method of simulating a prosthesis with a prosthesis simulator, comprising restraining one or more fingers of a wearer of the simulator, restraining a thumb of the wearer, and providing a plurality of artificial digits configured to move in a manner to simulate one or more prosthetic fingers and a prosthetic thumb of a prosthesis.

In any of the embodiments disclosed herein, the method can further comprise releasably attaching a cuff on a proximal end of the prosthesis simulator to the wearer, releasably restraining the one or more fingers to a first restraint attached to a roof plate of the prosthesis simulator, the roof plate connected to a base plate and defining a dorsal side of the prosthesis simulator device, and releasably restraining the thumb to a second restraint attached to a holster connected to the base plate on a palmar side of the prosthesis simulator opposite the dorsal side, wherein the plurality of artificial digits extends from the base plate on the palmar side of the prosthesis simulator device.

In any of the embodiments disclosed herein, the method can further comprise articulating the base plate relative to the cuff, the base plate comprising a joint connecting to the cuff, and articulating a rod connected to the joint thereby articulating the plurality of artificial digits.

In any of the embodiments disclosed herein, the first restraint can be slidably attached to the roof plate such that the first restraint can be positioned at varying distances away from the base plate.

In any of the embodiments disclosed herein, the plurality of artificial digits can be positioned in a 3 jaw chuck grasp.

In any of the embodiments disclosed herein, each of the plurality of artificial digits can comprise a polymer material and a silicone-based material.

In any of the embodiments disclosed herein, the one or more fingers can be one or more human digits scheduled to be amputated.

In any of the embodiments disclosed herein, the one or more fingers can be one or more healthy human digits.

Another example embodiment of the present disclosure can provide an amputation simulator device comprising a cuff on a proximal end of the amputation simulator device, the cuff configured to detachably attach to an arm of a wearer of the amputation simulator device, a roof plate hingedly coupled to the cuff and defining a dorsal side of the amputation simulator device, the roof plate comprising a first restraint configured to restrain one or more fingers of the wearer, a holster attached to the roof plate on a palmar side of the amputation simulator device opposite the dorsal side, the holster comprising a second restraint configured to restrain a thumb of the wearer, a plurality of artificial digits extending from the roof plate on the palmar side of the amputation simulator device, the plurality of artificial digits configured to move in a manner to simulate one or more prosthetic fingers and a prosthetic thumb of a prosthesis, and a rod connecting the plurality of artificial digits to the cuff.

In any of the embodiment disclosed herein, wherein the first restraint and the second restraint can be configured to immobilize one or more human digits.

In any of the embodiments disclosed herein, the plurality of artificial digits can be positioned in a 3 jaw chuck grasp.

In any of the embodiments disclosed herein, the first restraint can be slidably attached to the roof plate such that the first restraint can be positioned at varying distances away from the cuff.

In any of the embodiments disclosed herein, each of the plurality of artificial digits can comprise a polymer material and a silicone-based material.

Another example embodiment of the present disclosure can be a method of training an unaffected hand of a user with mobility restrained by a prosthesis simulator that matches a length of an unaffected anatomical arm of the user when worn using the unaffected hand to perform a task that an affected hand comprising a partially amputated hand can perform using a prosthesis comprising restraining portions of the unaffected hand in an open hand posture with the prosthesis simulator to restrain mobility of the unaffected hand comprising restraining one or more fingers of the unaffected hand of the user of the prosthesis simulator, and restraining a thumb of the unaffected hand of the user of the prosthesis simulator, and performing the task with at least one or more artificial digits of the prosthesis simulator, wherein the restraining and performing of the task by the unaffected hand trains the affected hand to perform the task with at least one or more prosthetic fingers and a prosthetic thumb of the prosthesis, wherein the one or more artificial digits form at least a portion of a three jaw chuck grasp with the thumb and the thumb is constrained at a right angle to and secured along a palm of the unaffected hard.

In any of the embodiments disclosed herein, the restraining portions of the unaffected hand in an open hand posture with the prosthesis simulator can further comprise releasably attaching a cuff on a proximal end of the prosthesis simulator to the user, wherein the restraining of the one or more of the fingers and thumb comprises releasably restraining the one or more fingers to a first restraint attached to a roof plate of the prosthesis simulator, the roof plate connected to a base plate and defining a dorsal side of the prosthesis simulator, and releasably restraining the thumb to a second restraint attached to a holster connected to the base plate on a palmar side of the prosthesis simulator opposite the dorsal side, and wherein the one or more artificial digits extend from the base plate on the palmar side of the prosthesis simulator.

In any of the embodiments disclosed herein, the performing can further comprise articulating the base plate relative to the cuff, the base plate comprising a joint connecting to the cuff, and articulating a rod connected to the joint thereby performing the task with at least one or more of the artificial digits.

In any of the embodiments disclosed herein, the first restraint can be slidably attached to the roof plate such that the second restraint can be positioned at varying distances away from the base plate.

In any of the embodiments disclosed herein, the prosthesis simulator can be a partial-hand prosthesis simulator, wherein the performing comprises opening of the artificial digits through wrist flexion and closing of the artificial digits through wrist extension, and wherein each artificial digit comprises a polymer material.

In any of the embodiments disclosed herein, the performing can further comprise articulating a base plate relative to a cuff, the base plate comprising a joint connecting to the cuff, and articulating a rod connected to the joint thereby performing the task with at least one or more of the artificial digits, and wherein the prosthesis simulator comprises a first restraint configured to restrain the one or more fingers of the user, a second restraint configured to restrain the thumb of the user, the one or more artificial digits, the cuff configured to detachably attach to an arm of the user, the base plate hingedly coupled to the cuff, thereby allowing the base plate to rotate relative to the cuff, and the rod, which connects the one or more artificial digits to the base plate, wherein an articulation of the base plate relative to the cuff causes articulation of the one or more artificial digits by the rod.

These and other aspects of the present disclosure are described in the Detailed Description below and the accompanying figures. Other aspects and features of embodiments of the present disclosure will become apparent to those of ordinary skill in the art upon reviewing the following description of specific, exemplary embodiments of the present invention in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAIL DESCRIPTION OF THE INVENTION

Figure 1A:
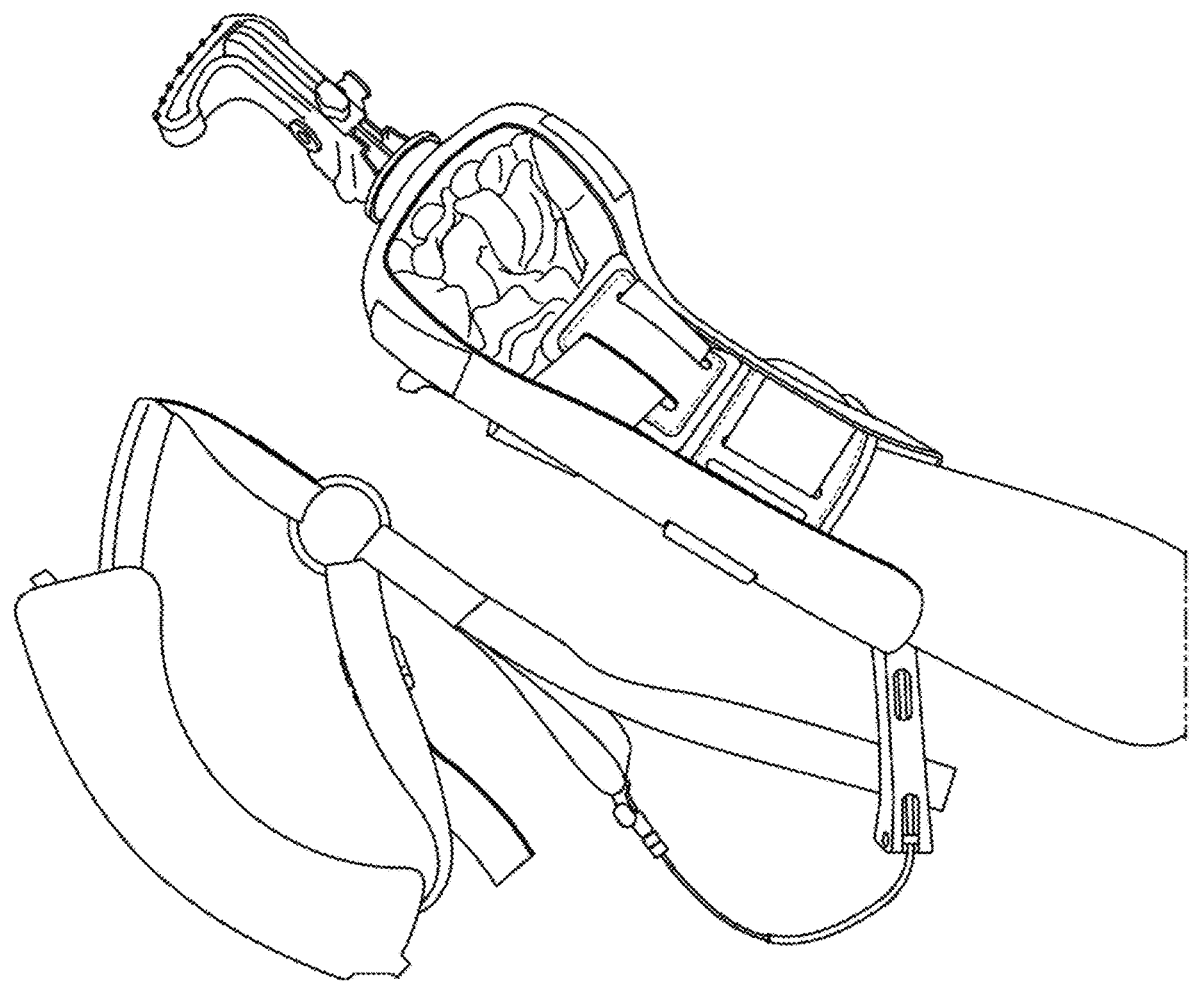
FIG. 1A illustrates a prosthesis simulator device of the prior art.

As described above, partial hand amputations account for over 90% of upper extremity amputations. Most commonly, a person has an amputation through the first three digits of their hand at the metacarpophalangeal (MCP) joint. In such cases, a partial hand prosthesis simulator is a device that can mimic the physical and functional properties of a prosthetic device that would be used by a person who undergoes such an amputation.

In the research space, the partial hand prosthesis simulator can provide a solution to immobilize fingers vital to grasp functions of the hand and replace them with prosthetic fingers suitable for grip. In such a manner, the simulator does not significantly lengthen the hand, which would cause a change in perception of arm length. In the clinical space, the simulator can provide a training mechanism for unilateral partial hand amputees. An amputee that is unable to be fit with a prosthesis on an affected hand can adapt to prosthesis use on an unaffected limb to learn critical adaptations that can convey to the affected side. The disclosed simulators can teach basic prosthesis motor skills necessary for device acceptance. This can allow users to be active in learning prosthesis skills instead of waiting for an injury or surgery to heal before training with the prosthesis device.

The disclosed devices do not extend the length of the limb, in contrast to many existing prostheses. The disclosed devices maintain limb length by placing the artificial fingers in positions similar to where they would be in an intact hand performing grasping actions. The disclosed devices can also limit tactile sensation and feedback from the immobilized fingers. This can allow for a better evaluation of how the device functions in comparison to someone with an amputation and a prosthesis.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

As used herein, the terms "prosthetic simulator," "prosthesis simulator," and/or "amputation simulator" are used interchangeably to refer to a partial hand prosthesis simulator as described above.

Figure 1C:
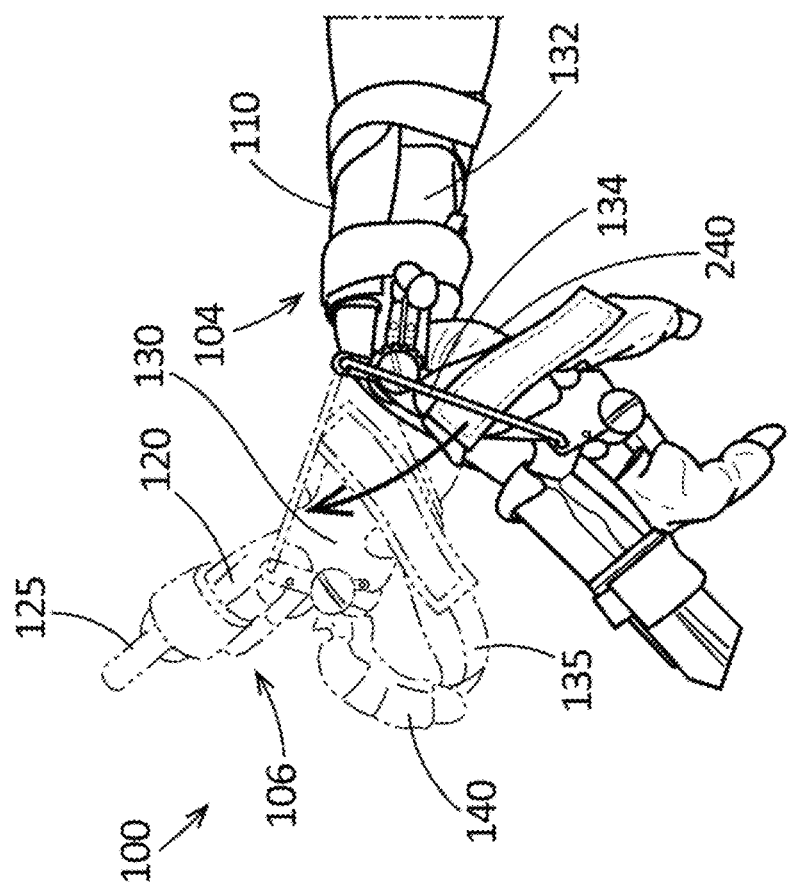
FIGS. 1B and 1C illustrate a prosthesis simulator device in accordance with some examples of the present disclosure.
Figure 1B:
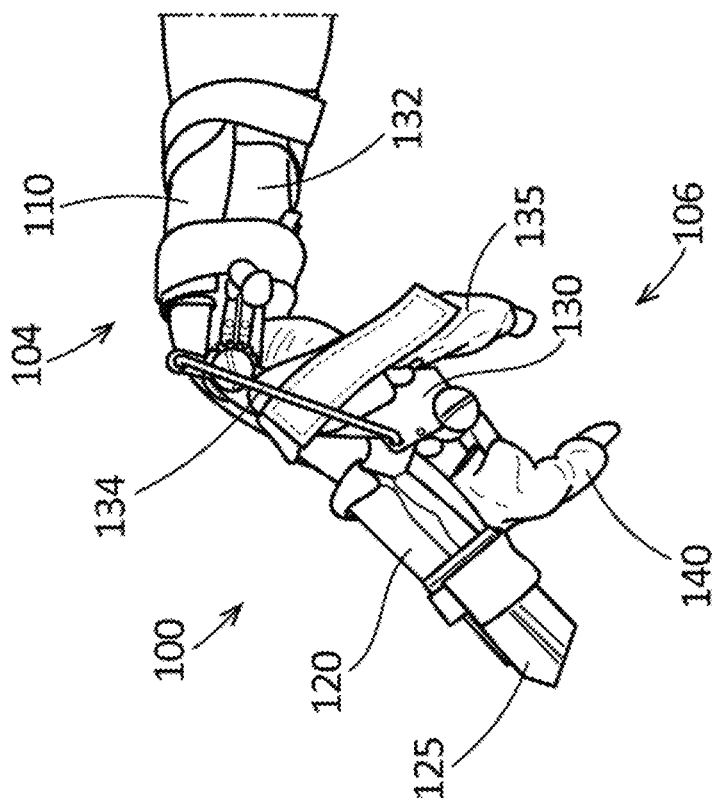

FIG. 1A illustrates an example of a prosthesis simulator of the prior art. FIGS. 1B and 1C illustrate an example of a prosthesis simulator device 100 in accordance with the present disclosure. As shown, the prosthesis simulator device 100 can comprise a cuff 110 on a proximal end 102 of the prosthesis simulator device 100. The cuff 110 can be configured to detachably attach to an arm of a wearer of the prosthesis simulator device 100.

The prosthesis simulator device 100 can further comprise a roof plate 120 hingedly coupled to the cuff 110 and defining a dorsal side 104 of the prosthesis simulator device 100. The roof plate 120 can comprise a first restraint 125 configured to restrain one or more fingers of the wearer. The first restraint 125 can be configured to immobilize the one or more fingers. The first restraint 125 can also be slidably attached to the roof plate 120 such that the first restraint 125 can be positioned at varying distances away from the cuff 110.

The prosthesis simulator device 100 can further comprise a holster 130 attached to the roof plate 120 on a palmar side 106 of the prosthesis simulator device 100. The palmar side 106 can be opposite the dorsal side 104. The holster 130 can comprise a second restraint 135 configured to restrain a thumb of the wearer. The second restraint 135 can be configured to immobilize the thumb.

Figure 2A:
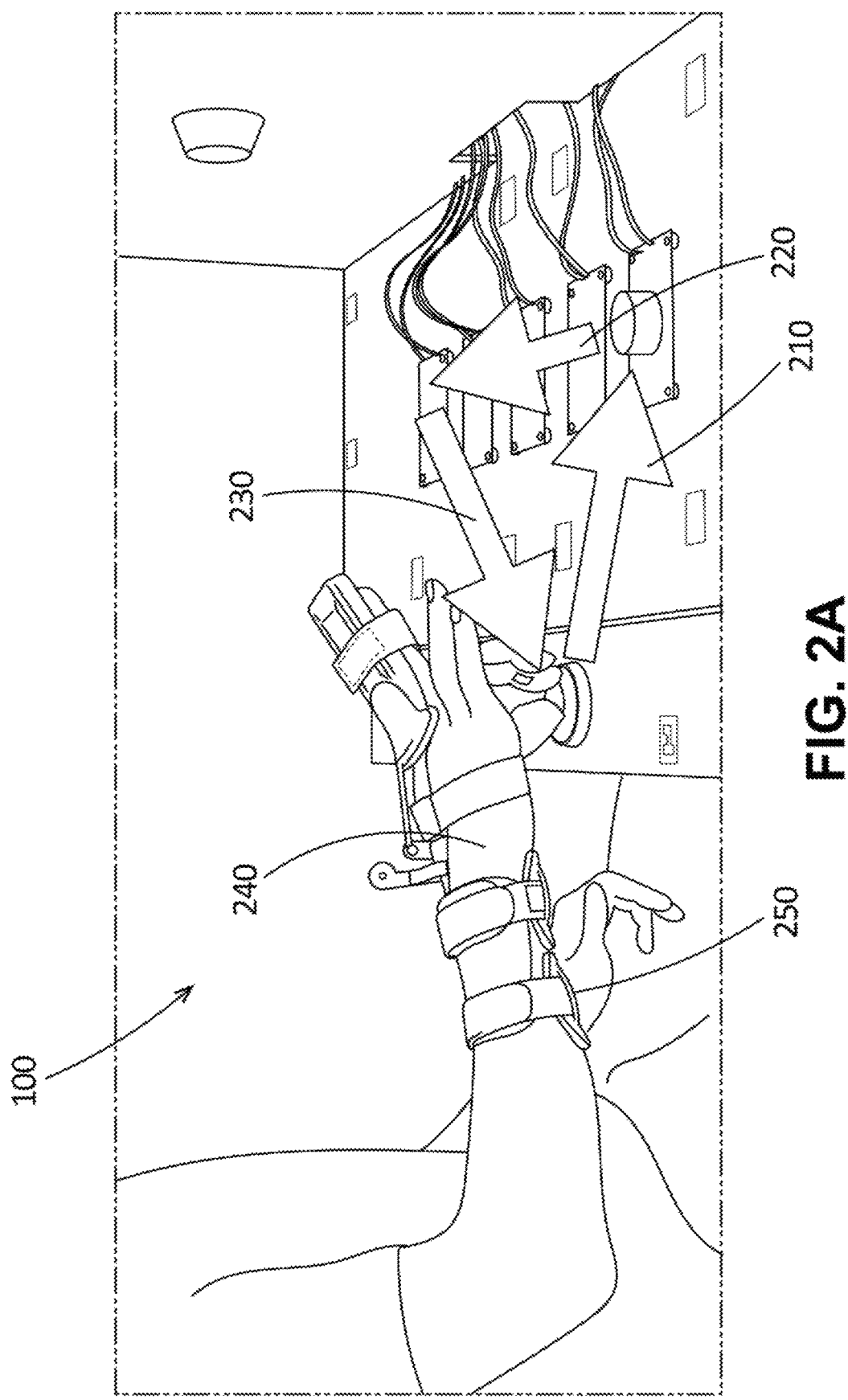
FIGS. 2A and 2B illustrate a prosthesis simulator device in accordance with some examples of the present disclosure.
Figure 2B:
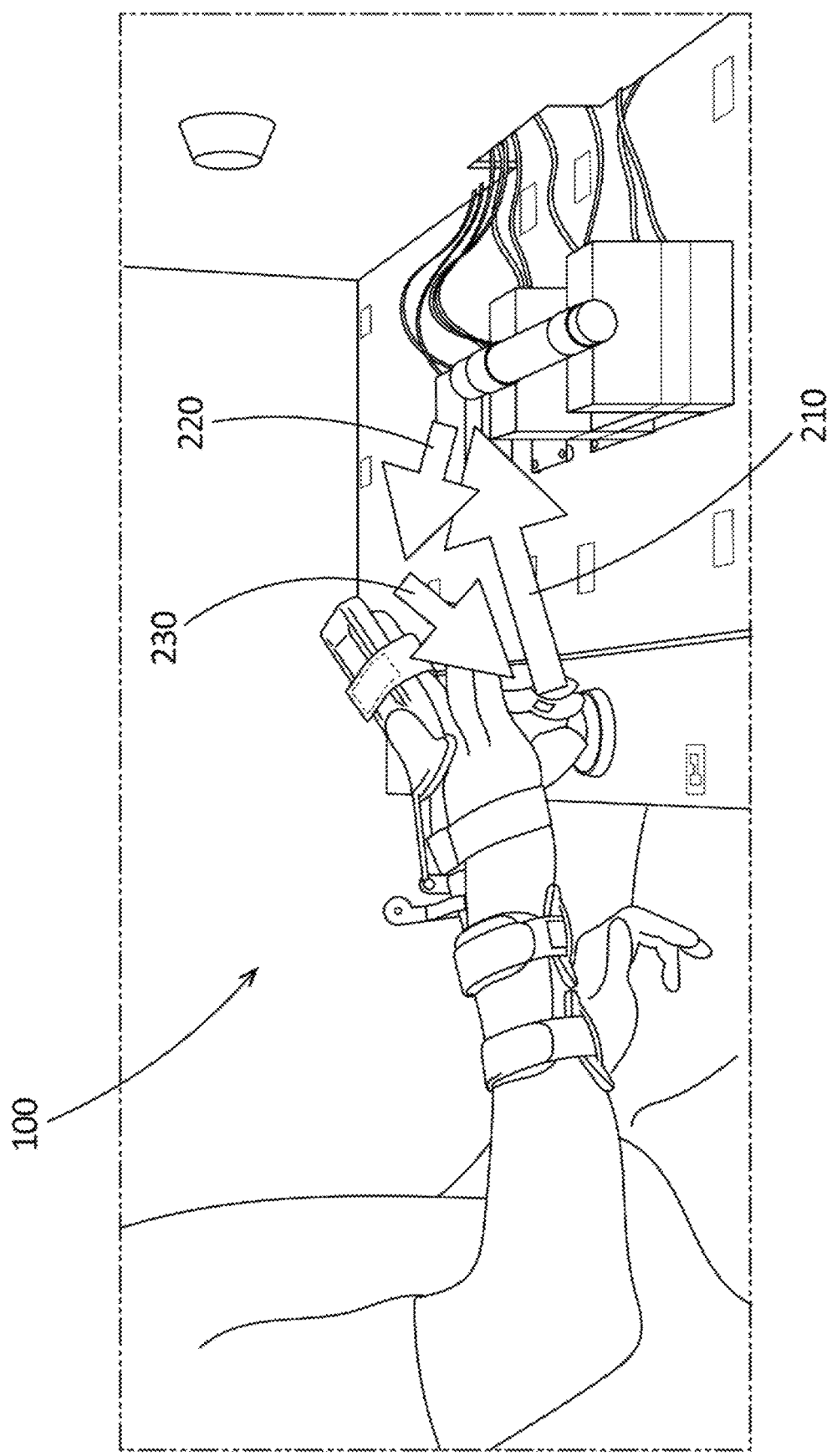
Figure 3A:
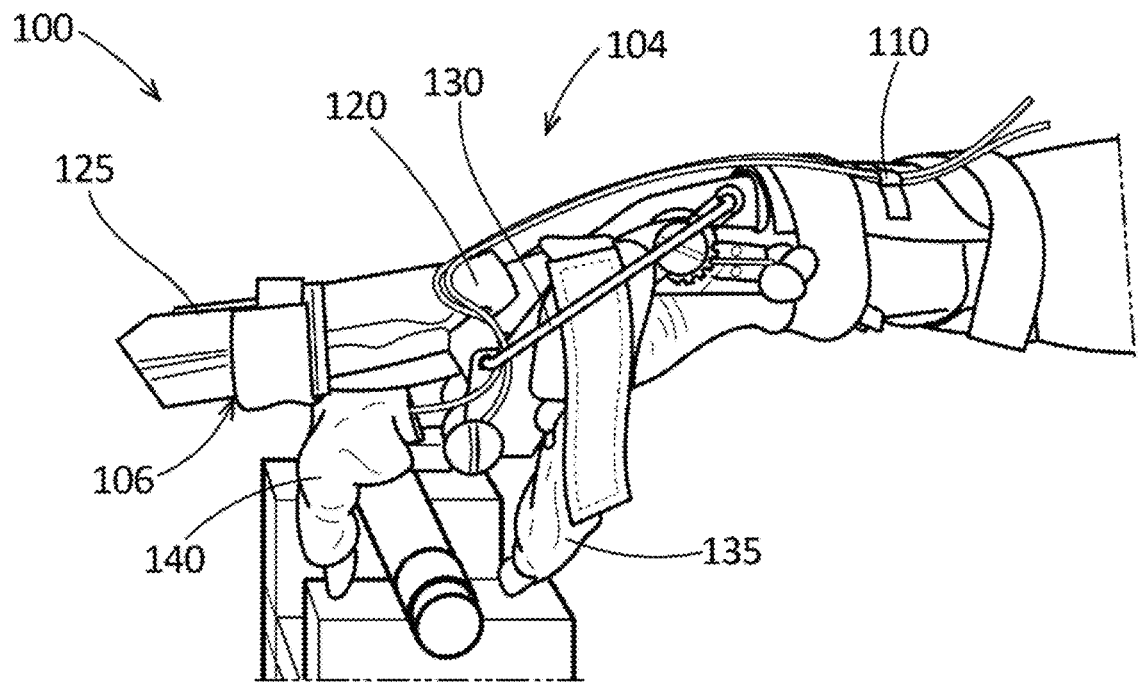
FIGS. 3A and 3B illustrate a prosthesis simulator device in accordance with some examples of the present disclosure.
Figure 3B:
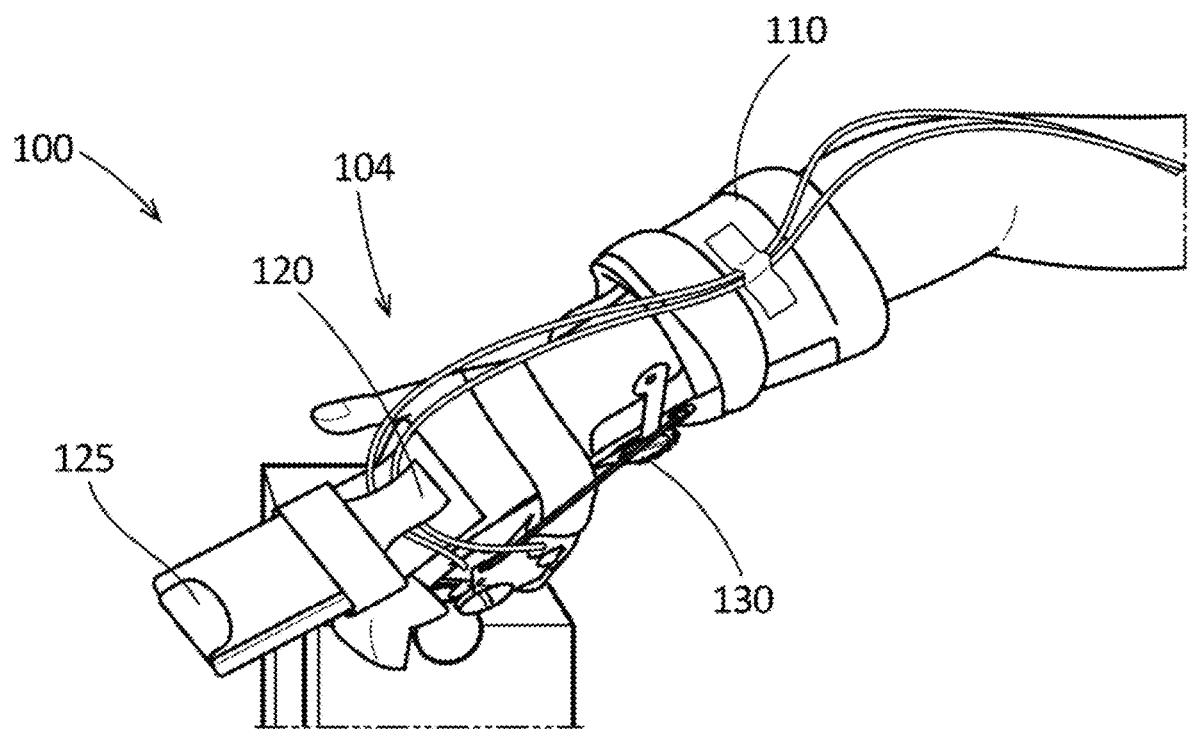

The prosthesis simulator device 100 can further comprise a plurality of artificial digits 140 extending from the roof plate 120 on the palmar side 106 of the prosthesis simulator device 100. The plurality of artificial digits 140 can be configured to move in a manner to simulate one or more prosthetic fingers and a prosthetic thumb of a prosthesis. For example, the plurality of artificial digits 140 can be positioned in a 3 jaw chuck grasp. Each of the plurality of artificial digits 140 can comprise a polymer material and a silicone-based material. Further examples of the prosthesis simulator device 100 are illustrated in FIGS. 2A, 2B, and 3A. FIG. 3B illustrates a prosthesis simulator of the prior art. Data relating to the performance of the prosthesis simulator device 100 relative to the prosthesis simulator devices of the prior art is shown in FIGS. 4A-7B. The method of use is illustrated in FIG. 8.

FIGS. 1B, 1C, and 2A further illustrate a method of training a first hand 240 with mobility restrained by the prosthesis simulator device 100 to perform a task that a second hand 250 can perform using the prosthesis comprising restraining portions of the first hand 240 in an open hand posture with the prosthesis simulator device 100 to restrain mobility of the first hand 240. The method comprises restraining one or more fingers of the first hand 240 of the wearer of the prosthesis simulator device 100 and restraining the thumb of the first hand 240 of the wearer of the prosthesis simulator device 100. The method further comprises performing the task with at least one or more artificial digits 140 of the prosthesis simulator device 100. The restraining portions of the first hand 240 in an open hand posture with the prosthesis simulator device 100 can further comprise releasably attaching the cuff 110 on the proximal end 102 of the prosthesis simulator device 100 to the wearer. Restraining of the one or more of the fingers and thumb can comprise releasably restraining the one or more fingers to the first restraint 125 attached to the roof plate 120 of the prosthesis simulator device 100, the roof plate 120 connected to a base plate 132 and defining the dorsal side 104 of the prosthesis simulator device 100 device. It can further comprise releasably restraining the thumb to the second restraint 135 attached to the holster 130 connected to the base plate 132 on the palmar side 106 of the prosthesis simulator device 100 opposite the dorsal side 104. The one or more artificial digits 140 can extend from the base plate 132 on the palmar side 106 of the prosthesis simulator device 100 device. Performing can further comprise articulating the base plate 132 relative to the cuff 110, the base plate 132 comprising the joint connecting to the cuff 110 and articulating a rod 134 connected to the joint thereby performing the task with at least one or more of the artificial digits 140.

Figure 8:
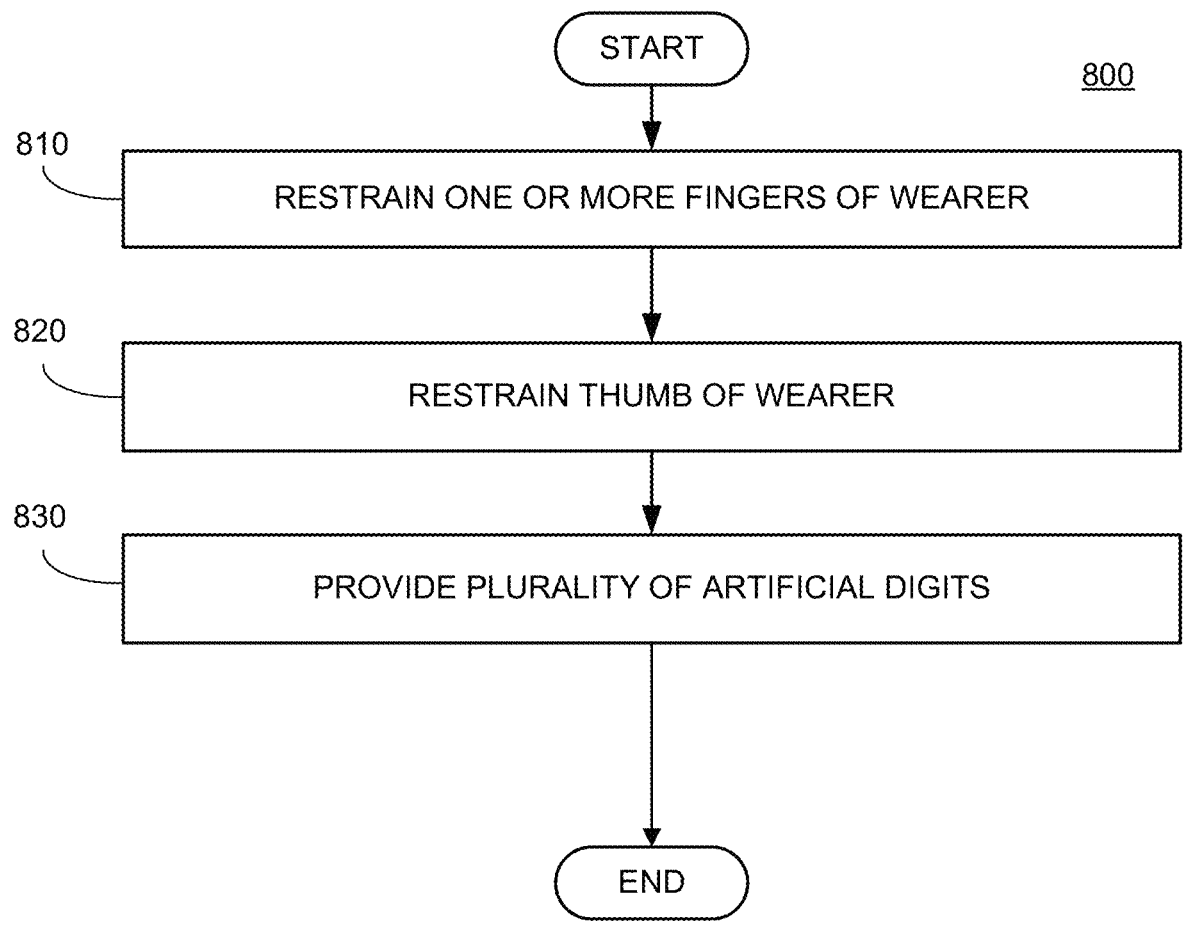
FIG. 8 illustrates a flow chart of an example method of simulating a prosthesis with a prosthesis simulator in accordance with some examples of the present disclosure.

FIG. 8 illustrates a method 800 of simulating a prosthesis with a prosthesis simulator 100. As shown in block 810, the method 800 can comprise restraining the one or more fingers of a wearer of the simulator. Block 810 can also include releasably attaching a cuff on a proximal end of the prosthesis simulator to the wearer. Block 810 can also comprise releasably restraining the one or more fingers to a first restraint attached to a roof plate of the prosthesis simulator. In block 820, the method 800 can comprise restraining a thumb of the wearer. Block 820 can further comprise releasably restraining the thumb to a second restraint attached to a holster connected to the base plate on a palmar side of the prosthesis simulator opposite the dorsal side. In block 830, the method 800 can comprise providing a plurality of artificial digits configured to move in a manner to simulate one or more prosthetic fingers and a prosthetic thumb of a prosthesis.

Goal-directed planning plays a pivotal role in how people perceive the requirements of a task to then engage the proper movements to achieve the desired outcome. Previous work has shown that task-specific demands influence how individuals grasp an object. In this disclosure, we evaluated whether level of prosthesis use or task difficulty influences motor adaptations in persons naïve to prosthesis use. Overall findings suggest that while partial-hand users may have more range in variability of how to grasp objects, such variability does not negatively influence functional adaptations, as defined here. As well, persons using partial-hand devices can have higher functional adaptability to their device than transradial device users when the task demands are more complex.

Grasp and object use are commonly discussed in terms of affordance. Affordances are an individual's perceived representation of an object within the context of its environment according to their ability to perform an action with (or on) that object. Thus, task dynamics consist of evaluating an object's affordance and implementing that conceptualised knowledge for the completion of the goal. When planning and implementing a grasp, participants must consider how the manipulation of the target object affects task-specific constraints. These demands grow even further when kinematics become altered from the natural. In amputation, the loss of extremity, and subsequent addition of a prosthesis, creates unique challenges to adapting grasps in goal-directed tasks. Both task demands and object affordances are greatly altered as individuals must now examine how their new effector can interact with the target object, as well as how they might be constrained in their ability to manoeuvre through the task environment.

Figure 5A:
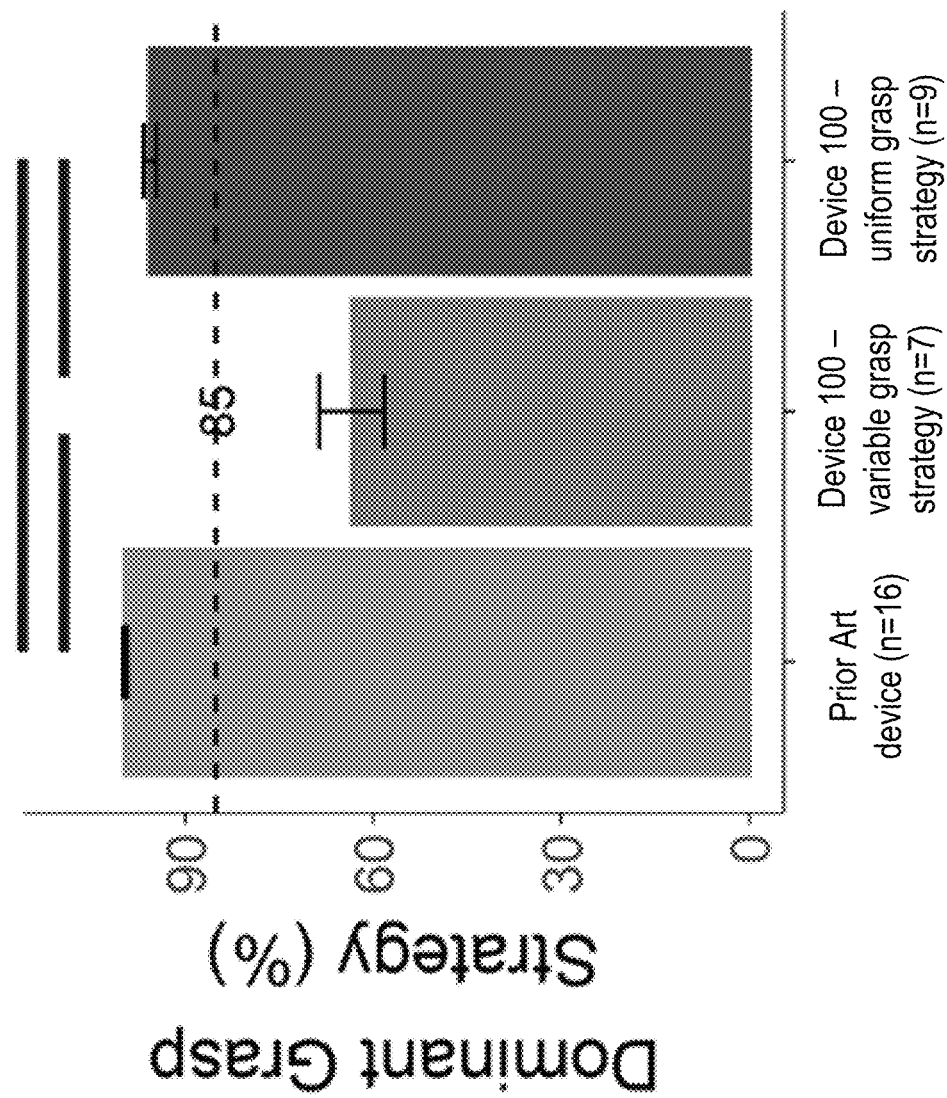
FIGS. 5A and 5B illustrate bar graphs demonstrating the difference between grasp strategy using a prosthesis simulator device in accordance with some examples of the present disclosure.

As all participants were naïve to prostheses, participants had to effort an understanding of how to best operate the device based on the expected task outcome. In this disclosure's tasks, the Translation task showed a clear pattern of performance that suggested one main primary grasp, regardless of prosthesis. However, the addition of rotation compelled some PhPS participants to utilise different approaches to perform the task. Research suggests that such variability may arise from the exploration-exploitation dilemma, wherein a participant must weigh the cost of exploring new strategies or exploiting those with known outcomes. Participants either plan their initial grasp strategy to match the precision demands of the task, or they use previously successful grasp strategies to reduce cognitive demand, regardless of precision requirements. These changes in grasp strategy rely on action semantics (e.g., conceptual knowledge, object knowledge, action-oriented representations), as goal-directed movements require both basic processes of motor control such as action planning and knowledge of object use, as well as higher-level processing of semantic knowledge. This variability may play an important role in motor learning and rehabilitation, where with increased repetition—as more kinematic information becomes available—exploration decreases, and participants exhibit higher repeatability. Based on the findings in this disclosure, stabilisation of grasp strategy did not occur during the Rotation task (FIG. 5A). It is possible that with further repetition, variability will decrease causing more participants to trend towards the uniform group. Future studies can explore if more trials of the task allow for selection/deselection of certain grasp strategies, or if grasp strategy is influenced through the course of rehabilitation. The demands of the Rotation task bear similarity to the concept of end-state comfort, where grasp strategy is planned based on the comfort of the final hand position. End-state comfort requires an awkward initial grasp to later implement the action comfortably and efficiently. In the Rotation task, if a PhPS user grasps the marker from the top, it requires an awkward forearm rotation with shoulder elevation to accomplish the task. Grasping from the side only requires forearm rotation.

Device level can also impact limb degrees of freedom. Partial-hand users have more degrees of freedom of movement, whereas transradial users are more constrained by the functioning of the device. Present results suggest that with low task complexity (in the Translation task), participants have no obvious incentive to employ multiple grasp strategies, thereby reducing the effects between device level on grasp strategy and performance. However, when task complexity is increased in the Rotation task, it encourages partial-hand users to explore multiple grasp postures to optimise movement and performance, leading to stratification in strategy. It is possible that transradial users fall into a "forced uniform" group as the TrPS constrains forearm rotation, limiting opportunities to have much choice of grasp strategy in either task performed here. It is unclear how that constraint may affect other behaviours which may necessitate different joint and body movements.

When there is a ceiling in task difficulty, despite differences in DoF between devices, the lack of significant differences in movement duration suggest that device-induced constraints may not impact motor adaptation. When difficulty is increased, it is possible that device-induced constraints on variability may hinder motor adaptation. This is particularly intriguing as there is a non-significant difference in strategy use between the transradial and partial-hand groups in this task. This further supports that prosthesis level and task demands should be considered in prosthesis research moving forward.

Examining reach peak velocity, data suggest that task demands, and device constraints may play an even larger role in movement outcomes. In the Rotation task, uniform and variable partial-hand groups show consistent significant increases in velocities across trial bins. This effect is largely absent in the Translation task. This may perhaps again be attributed to a ceiling effect in difficulty. When task demands are low, there is less impetus on improving adaptation to mitigate device constraints as the maximum performance is already achieved. As task demands increase, adaptation to device constraints becomes an integral factor in improving functional performance.

In the Rotation task, in addition to increases in peak velocity over time in the partial-hand groups, there are significant differences in reach peak velocities between transradial and partial-hand users within trial bins. This may indicate that movement variability is an important player in motor kinematics. Despite the fact that there are no significant differences in the peak velocities between the partial-hand uniform and variable groups, it may be that even the potential for kinematic variability is vital for motor learning during prosthesis use and may play a vital downstream role in motor learning and rehabilitation.

Certain embodiments and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

EXAMPLES

Thirty-three (33) right-handed, healthy adults (age=22.64±3.17 years; 15 female) with intact upper extremities were recruited to participate in the study. All participants provided written, informed consent, and the Georgia Institute of Technology Institutional Review Board approved all methods. Participants completed the Edinburgh Handedness Inventory to confirm right-handedness. Participants were placed pseudo-randomly into either the transradial (n=17) or partial-hand (n=16) prosthesis simulator group.

Participants performed the experimental tasks wearing a prosthesis simulator that fit over their intact right extremity. The transradial prosthesis simulator (TrPS) (prior art device) mimics a below-elbow amputation including the hand and wrist by restricting pronation and supination of the wrist joint. The palm of the hand is padded with soft fabric to maintain an open hand posture, thereby limiting sensory control and feedback. The TrPS features body-powered opening via a figure-of-nine harness that allows for voluntary opening of the split-hook end-effector through glenohumeral flexion and scapular/bi-scapular abduction (FIG. 1A).

The partial-hand prosthesis simulator (PhPS) (device 100) mimics the loss of digits 1-3 (thumb, forefinger, and middle finger) at the metacarpophalangeal joint, a common partial-hand amputation. The thumb is constrained at a right angle secured along the palm, and the fore and middle fingers are strapped to a roof plate just proximal to the distal joint of each finger. The PhPS functions via body-powered opening though wrist flexion and closing through wrist extension (FIGS. 1B, 1C).

Participants were seated in a chair before a custom-built experimental apparatus (FIGS. 2A, 2B). Custom, copper-printed circuit boards (task "targets") with concentric electroconductive rings were created to establish behavioural measures of accuracy and movement duration programmed using an Arduino Due. Conductive aluminium tape was applied to the bottom of task objects to ensure full contact with the rings conveying information about when an object was placed onto or removed from the circuit, and with which ring the object was in contact. Arduino was further used for event-marker synchronisation with the motion capture system.

Ascension 3D Guidance TrakStar™ was used for electromagnetic motion capture to collect 3-dimensional positional data using sensors taped to both sides of the end-effector of the prosthesis simulator. This system uses an electromagnetic pulse to monitor sensor position in relation to a transmitter reference. Nine anatomical landmarks were denoted for each participant to allow for digitisation of segment lengths using the local coordinate system: (1) C7/T1, (2) acromioclavicular joint, (3) Trigonum spinae, (4) angulus inferior, (5) angulus acromialis, (6) coracoid process, (7) approximated ulna, (8) approximated radius, (9) top of the fixed jaw of the end effector. Data were collected using The MotionMonitor software system at a sampling rate of 100 Hz. Data were exported to MATLAB (The MathWorks Inc., Natick, MA) for registration of task progression, data collection, and further analysis.

All participants completed two reach-to-grasp tasks with differing levels of difficulty and kinematic complexity using either the TrPS or NIPS on their right extremity. Both tasks mimic aspects of the Action Research Arm Test (ARAT), which is a common assessment of upper-extremity function, and categorises tasks by action type (grasp, grip, pinch, and gross movement) and performance difficulty. Here, tasks involve object translation and rotation and spatiotemporal precision, while accounting for object-specific properties such as shape, weight, and object material.

Participants were read scripted verbal instructions on how to perform each task and were asked to complete actions as quickly and accurately as possible. They were instructed to begin by depressing a button using the simulator at the start position. Once pressed, the button illuminates. After a set interval of 7 seconds, the light turns off, serving as the "Go" signal to begin the action. Participants were instructed to reach and grasp the task object, lift, and place it on the target position, then return to the start position. After returning to the start position, the light came back on as the wait signal for the next movement. An experimenter reset the task board at the completion of each movement. After verbal instructions, participants viewed a video of an actor properly completing 1 trial of the task using the prosthesis simulator from a sagittal perspective. Participants were not given information regarding how to use either prosthesis simulator.

The object in the simple ("Translation") task is a small metal disk Participants were instructed to reach and grasp the metal disk before translating it to a target position (FIG. 2A) One trial consists of four movements and participants completed 20 trials of this task, for a total of 80 movements.

The task object in the complex ("Rotation") task is a marker sitting horizontally in a cradle. Participants were instructed to reach and grasp the marker by the cap, then make a translation and rotation before placing it vertically, standing on its end at the target position (FIG. 2B). One trial consists of two movements and participants complete 20 trials of this task, for a total of 40 movements. This task is particularly challenging for prosthesis users. In particular, the rotational component is compromised using the TrPS, due to the immobilisation of the wrist joint. Additionally, this task requires rotation without tactile knowledge of grasp security for both the TrPS and PhPS.

Participants began with the Translation task then were given 5 minutes of rest before engaging in the Rotation task.

Figure 3C:
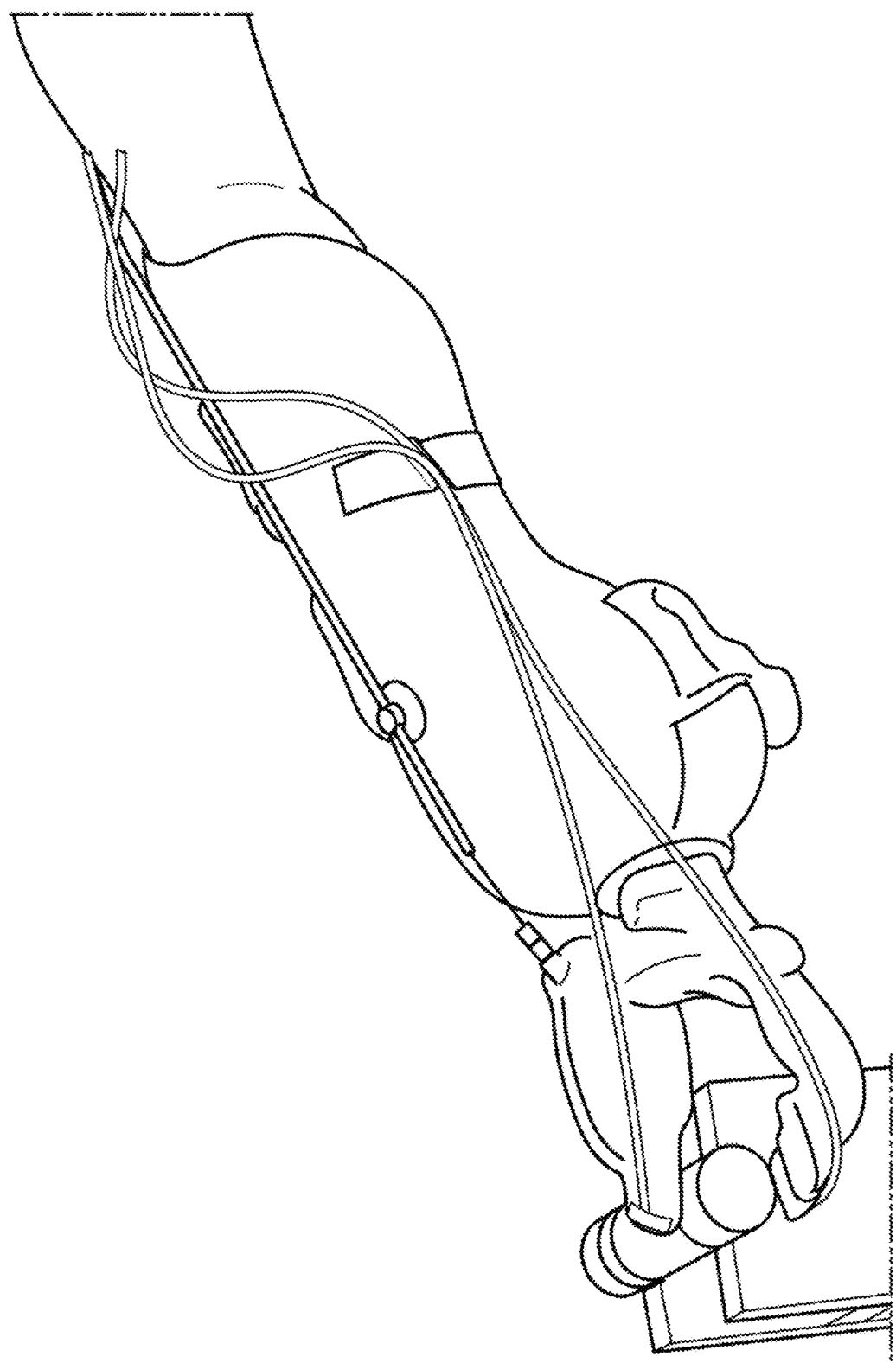
FIG. 3C illustrates a prosthesis simulator device of the prior art.

As the prosthesis simulators employed constrain different degrees of freedom, participants were not constrained to grasp the objects in any specific way. Visual identification was used to evaluate reach-to-grasp performance for each movement by a rater (SA), which was independently verified (BA). Based on this visual analysis, it was apparent that some users performed different methods of reach-to-grasp (i.e., "grasp strategy"). Primarily, PhPS users would either grasp the target object from above or would rotate their arm 90° and grasp the target object sideways (FIGS. 3A, 3B). TrPS users generally relied on the same strategy of the sideways grasp (FIG. 3C). Further, some PhPS users preferred to use the same grasp strategy for every movement, while others changed how they performed the reach-to-grasp across different movements. Based on these behavioural patterns, if a participant grasped the task object with the same grasp strategy for >85% of grasps, they were classified as uniform. Participants using a single grasp strategy for <85% of their grasps were classified as variable.

Movement duration was quantified as the time in milliseconds from the initiation of reach, indicated by the release of the start position button after the "Go" signal, to when the participant returns and presses that button after completion of the movement. Video recordings were used to confirm rejection of trials when a participant dropped the object.

As reaching movements followed a well-identified bell-shaped velocity profile, reach peak velocity was found using the findpeaks function in MATLAB from the motion capture data by plotting velocity profiles over time for each movement, which were then visually confirmed.

By inverting the data and re-utilising the findpeaks function, reach duration was calculated as the time in milliseconds between the velocity minima immediately preceding and following the reach peak velocity.

While object placement onto the centre ring was not an explicit requirement of the task, placement error was gauged by recording how centrally the test object was placed onto the targets. This outcome is quantified by recording onto which of the three concentric rings the test object was placed on the target circuit boards. The central ring has a diameter of 30 mm, the middle ring has a diameter of 40 mm, and the outer ring has a diameter of 60 mm. Objects placed on the central ring were recorded as "Error 0". When placed on the middle or outer ring, data were recorded as "Error 1" or "Error 3", respectively. This allowed for proper weighting of placement error as the distance between the middle and outer rings is twice the distance between the inner and middle rings.

Two participants were removed from the study. For one participant, a technical error caused the loss of data for the Rotation task. The second participant was removed as they exhibited uniquely abnormal movement patterns in the Translation task.

All statistical analyses were conducted using RStudio 2009-2019 version 1.2.5033. All data were subjected to a Shapiro-Wilk test to determine normality. Dominant grasp strategy data were tested using a Kruskal-Wallis rank sum test followed by a Dunn's Test with Benjamani-Hochberg procedure to control for false discovery rate. A p-value<0.05 was considered significant. Epsilon squared calculations using R were used to assess effect size, and $\varepsilon^2 > 0.8$ was considered a large effect size.

Linear mixed effects models were used to determine the contribution of fixed effects (group and trial bin) in the data. A null model was created using the lme function to examine baseline differences in outcome measures containing only the random effect of participant. Further models incorporated each of the fixed effects individually before evaluating the combination of fixed effects to determine the main and interaction effects. An ANOVA was then caned out to evaluate the differences between means of the data. Post-hoc pairwise comparisons were calculated using the lsmeans function for a Tukey's Test and the emmeans function with Bonferroni correction for multiple comparisons.

Figure 4A:
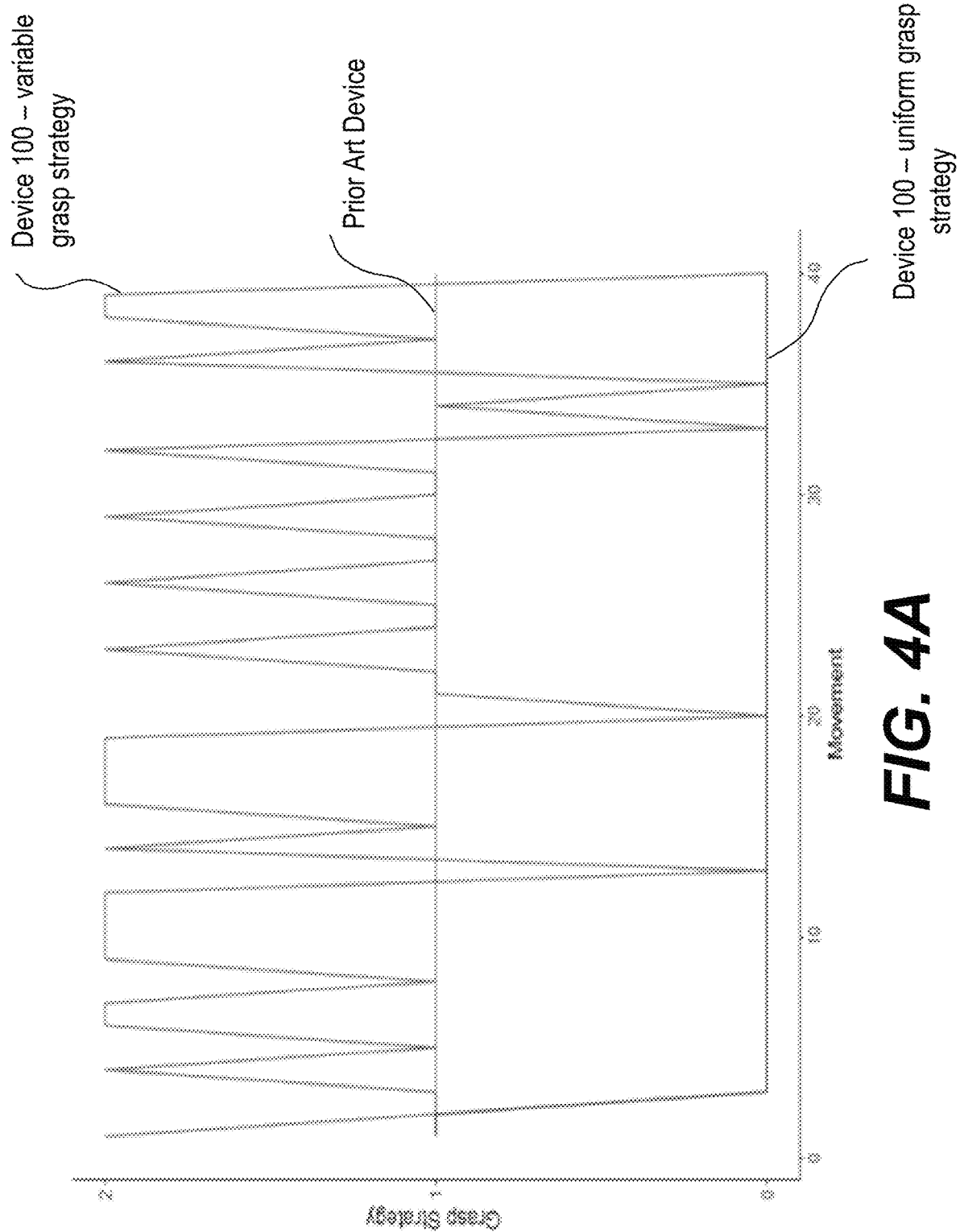
FIG. 4A illustrates a representative plot of grasp strategy with repetition for a single participant using a prosthesis simulator device in accordance with some examples of the present disclosure.

In the Rotation task, behavioural results showed a stratification of PhPS users into two groups: (1) those who maintained a persistent, uniform grasp strategy throughout the testing session, and (2) those who utilised multiple (variable) grasp strategies. FIG. 4A shows the variability in grasp strategy for a representative participant within each strategy group. Dominant grasp strategy was examined for each participant (FIG. 4B) during the Rotation task. These data are the basis for stratifying participants in groups based on dominant grasp strategy.

The Rotation task showed a significant main effect of group ($\chi^2$ (2)=25.198, p=3.375×10$^{-6}$, $\varepsilon^2$=0.81) (FIG. 5A). TrPS users showed significantly higher dominant grasp strategy than both the PhPS Uniform group (p<0.01) and the PhPS Variable group (p=3.101×10$^{-6}$). Both PhPS groups were also significantly different from each other, with the PhPS Uniform group showing significantly higher dominant grasp strategy than the PhPS Variable group (p<0.03).

Figure 5B:
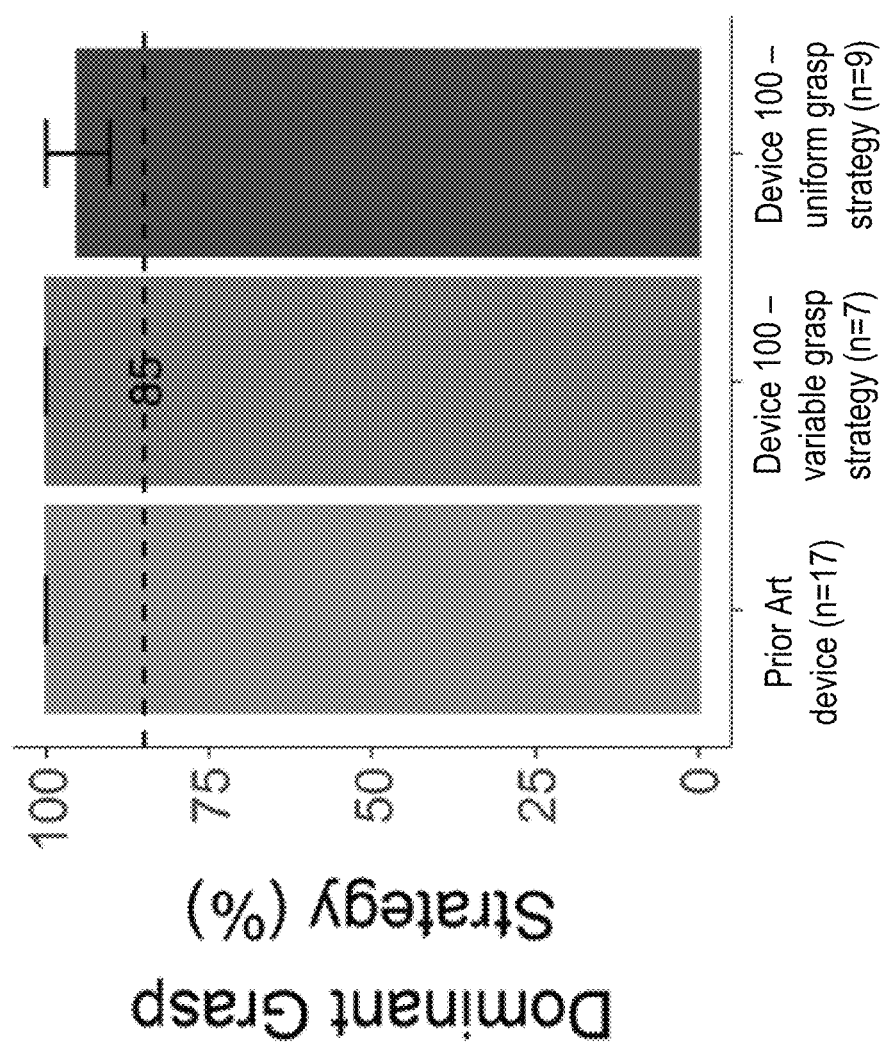

Strategy groupings seen in the Rotation task were maintained for analysis of the Translation task. This permitted comparisons of participants with uniform grasp strategy and variable grasp strategy across different levels of task complexity. These dominant grasp strategy groupings were maintained across both tasks for all performance measures. In the Translation task, there was not a main effect of group ($\chi^2$ (2)=2.667, p=0.264), indicating consistently uniform grasp strategies (FIG. 5B).

To examine how functional adaptation differs between device levels, we evaluated whether movement duration is sensitive to device level and task difficulty.

Figure 6A:
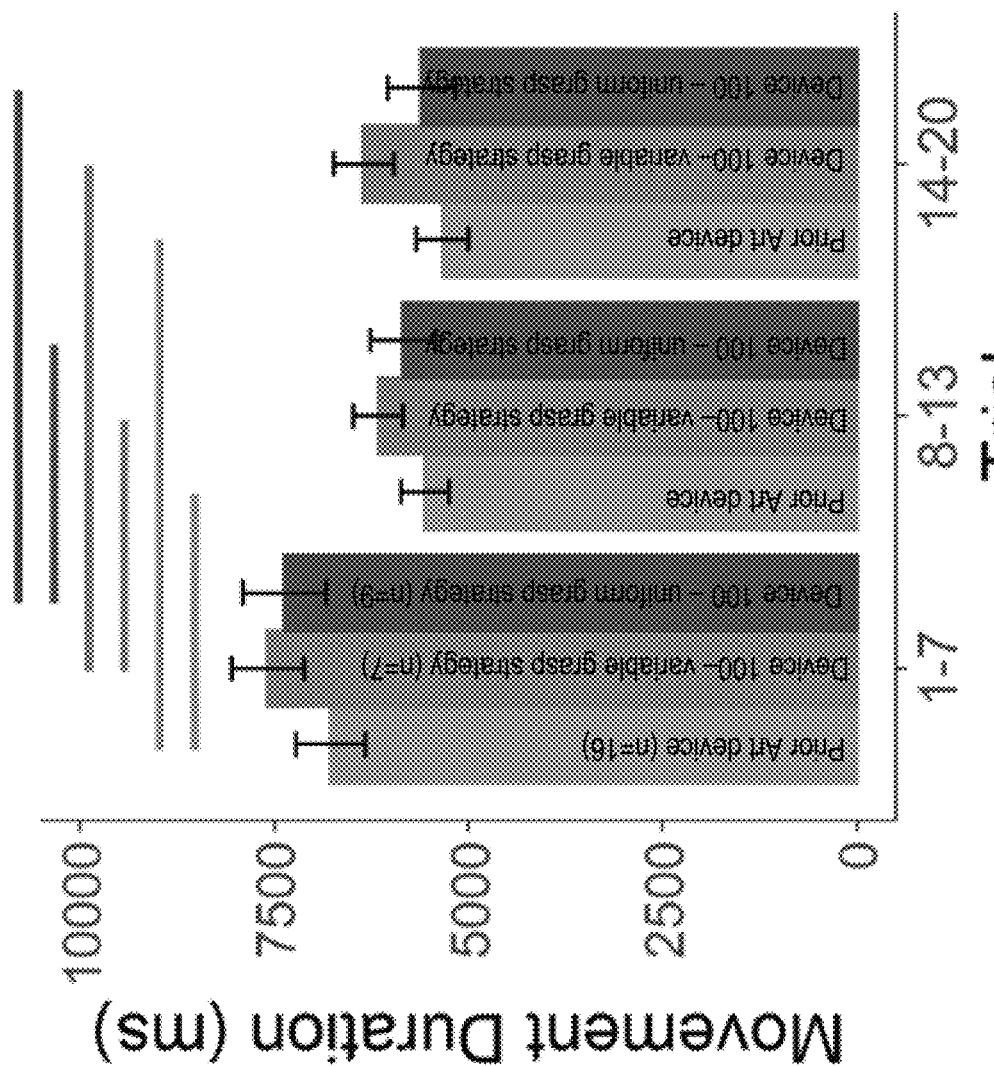
FIGS. 6A and 6B illustrate bar graphs demonstrating the movement duration using a prosthesis simulator device in accordance with some examples of the present disclosure.

In the Rotation task, there was a significant main effect of trial bin (p<0.0001) and a significant interaction effect of group×trial bin (p<0.0001). In the TrPS group, movement duration showed a significant decrease between the first and second trial bins (p<0.0001), and between first and third trial bins (p<0.0001) (FIG. 6A).

In the PhPS Variable group, movement duration showed a significant decrease between the first and second trial bins (p=0.0012), and between first and third trial bins (p=0.0084).

In the PhPS Uniform group, movement duration showed a significant decrease between the first and second trial bins (p=0.0001), and between first and third trial bins (p<0.0001).

Figure 6B:
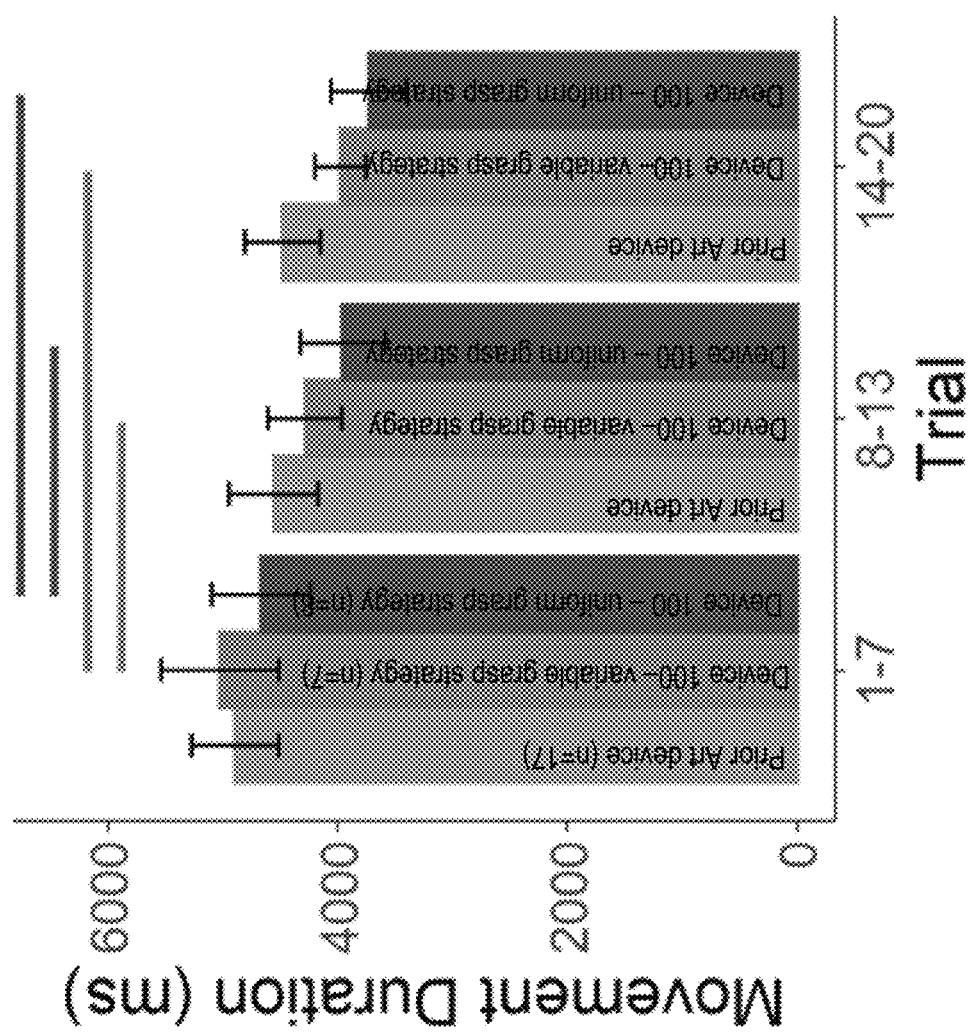

In the Translation task, there was a significant main effect of trial bin (p<0.0001) and a significant interaction effect of group×trial bin (p<0.0001) (FIG. 6B).

In the PhPS Variable group, movement duration showed a significant decrease between the first and second trial bins (p=0.0194), and between first and third trial bins (p=0.0001).

In the PhPS Uniform group, movement duration showed a significant decrease between the first and second trial bins (p=0.015), and between first and third trial bins (p=0.0003).

Differences in reach duration may reflect how individuals decide which grasp posture to employ as well as their variability in utilising that posture.

In the Rotation task, there was a significant main effect of trial bin (p=0.0051) and a significant interaction effect of group×trial bin (p<0.0057). Reach duration showed a significant increase between the first and second trial bins for the TrPS group (p=0.0168).

For the Translation task, there were no significant main effects for device, group, or trial bin. Nor were there significant interaction effects.

Similar to reach duration, differences in reach peak velocity may identify how decisions about the grasp posture and variability affect movement outcomes.

Figure 7A:
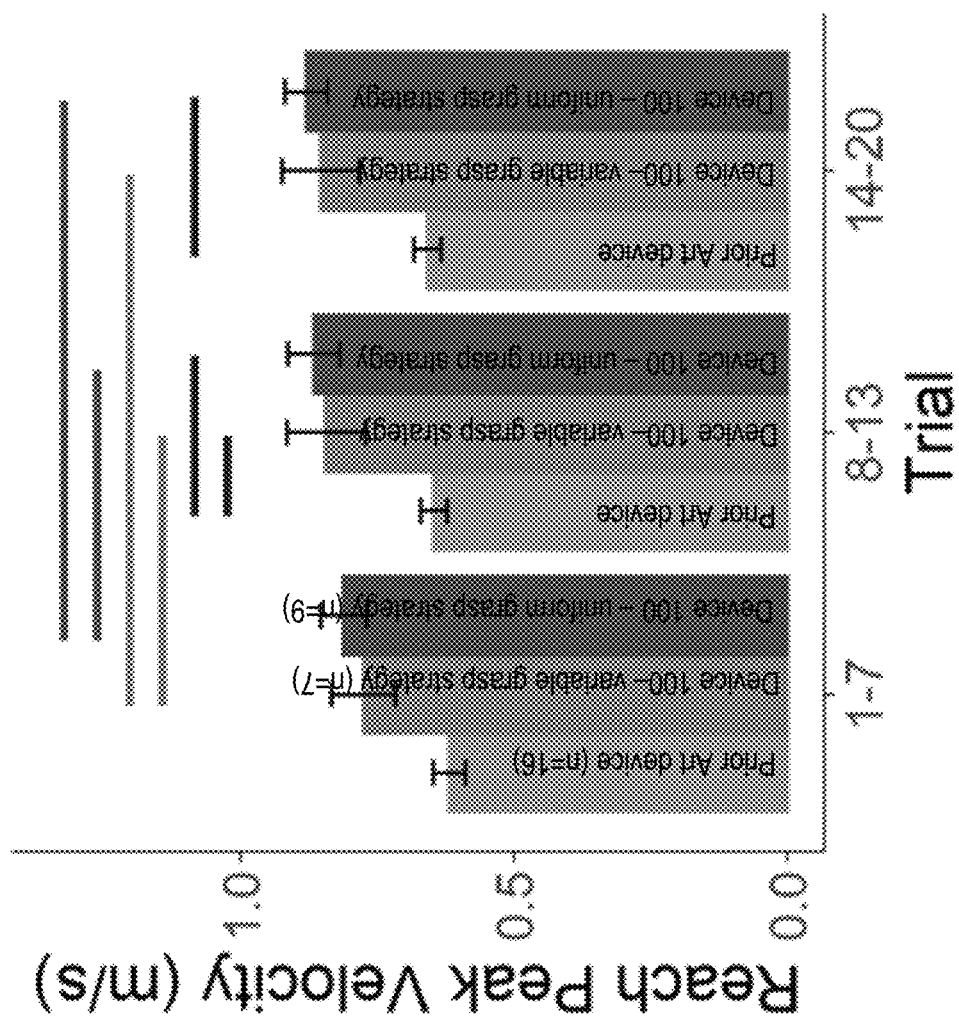
FIGS. 7A and 7B illustrate bar graphs demonstrating the reach peak velocity using a prosthesis simulator device in accordance with some examples of the present disclosure.

In the Rotation task, there were significant main effects of group (p=0.0005) and main effects of trial bin (p<0.0001) (FIG. 7A).

In the PhPS Variable group, reach peak velocity showed a significant increase between the first and second trial bins (p=0.0331), and between first and third trial bins (p=0.0095).

In the PhPS Uniform group, reach peak velocity showed a significant increase between the first and second trial bins (p=0.0182), and between first and third trial bins (p=0.0017).

Additionally, both the PhPS Uniform (p=0.0091) and the PhPS Variable (p=0.0484) groups showed significantly higher reach peak velocities than the TrPS group in the second trial bin.

The PhPS Uniform group also showed significantly higher reach peak velocity than the TrPS group (p=0.0078) in the third trial bin.

Figure 7B:
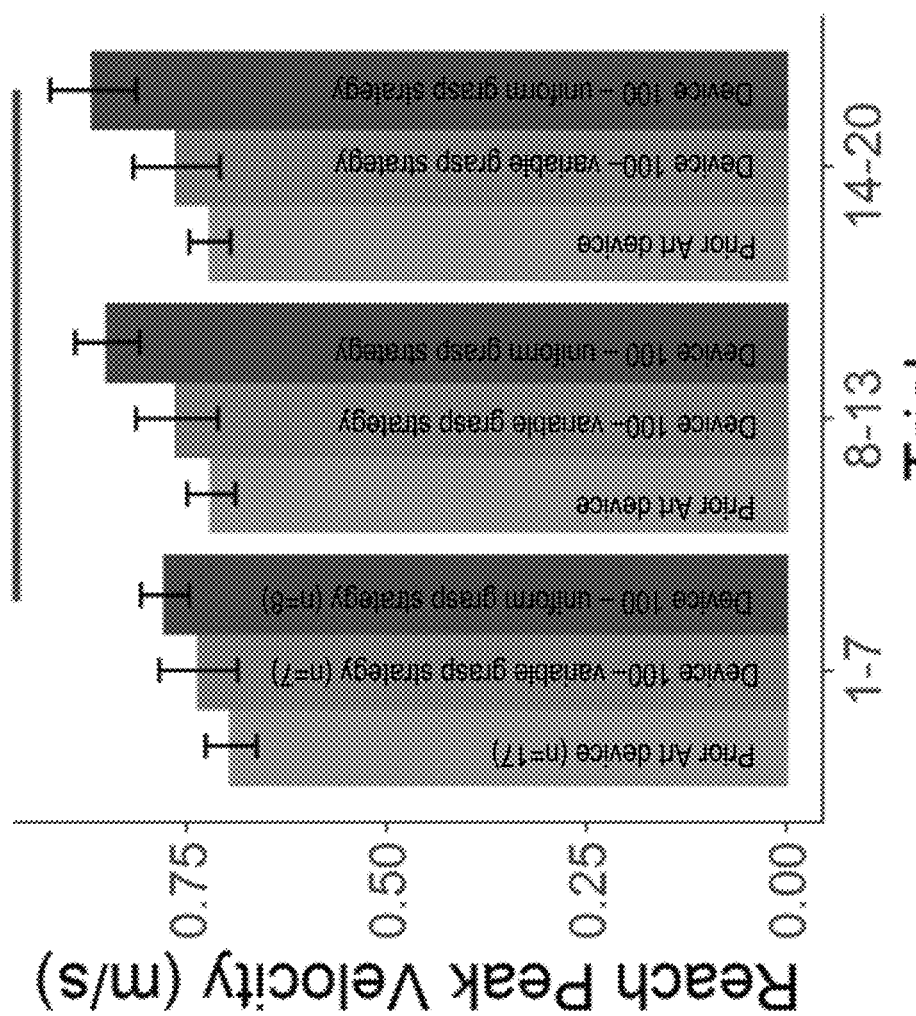

In the Translation task, there was a significant main effect of trial bin (p=0.0015). The PhPS Uniform group showed a significant increase in reach peak velocity between the first and third trial bins (p=0.0123) (FIG. 7B).

FIG. 1A: TrPS: This orthosis simulates a transradial amputation by encompassing the hand, wrist, and forearm. It features a voluntary opening of a split-hook effector via a figure-of-nine harness operated through glenohumeral flexion and scapular/bi-scapular abduction. Padding placed in the palm limits sensory feedback and control. FIGS. 1B, 1C: PhPS: This orthosis mimics a partial-hand amputation of the first three digits. The thumb is constrained at a right angle along the palm, while the fore- and middle fingers are secured to a roof plate to limit sensory feedback and control. The PhPS operates through voluntary opening and closing via wrist flexion and extension, respectively. TrPS: transradial prosthesis simulator, PhPS: partial-hand prosthesis simulator.

FIG. 2A: The participant is seated at the experimental setup wearing the PhPS and completing the Translation task. This task requires a reach-to-grasp (arrow 210) to pick up a small metal disk. The disk is then translated (arrow 220) to a target location where it is placed. The participant then returns to the starting position (arrow 230). FIG. 2B: The participant is completing the Rotation task. This task follows the same structure as the Translation task but requires the additional requirement of rotating the marker to place it vertically on its end at the target location (arrow 220). The target circuit board is comprised of three concentric rings. If the object is placed on the innermost ring, no error is recorded. If the object is placed touching the middle ring, it is recorded as Error 1. If the object is placed touching the outermost ring, it is recorded as Error 3, as the distance from the middle ring to the outer ring is twice as far as the distance from the inner ring to the middle ring. This schematic conveys the process of completing each task. Participants begin by pressing a button at the start position for 7 seconds, then are given a "Go" signal. On that signal, participants complete the reach-to-grasp, translation (and rotation for the Rotation task), and return. Once they return to the start position, they press the button and repeat the cycle for 20 trials.

FIG. 3A: Demonstration of a participant grasping the object from above using the PhPS. FIG. 3B: Demonstration of a participant grasping the object from the side using the PhPS. FIG. 3C: Demonstration of a participant using the TrPS to grasp the object.

Figure 4B:
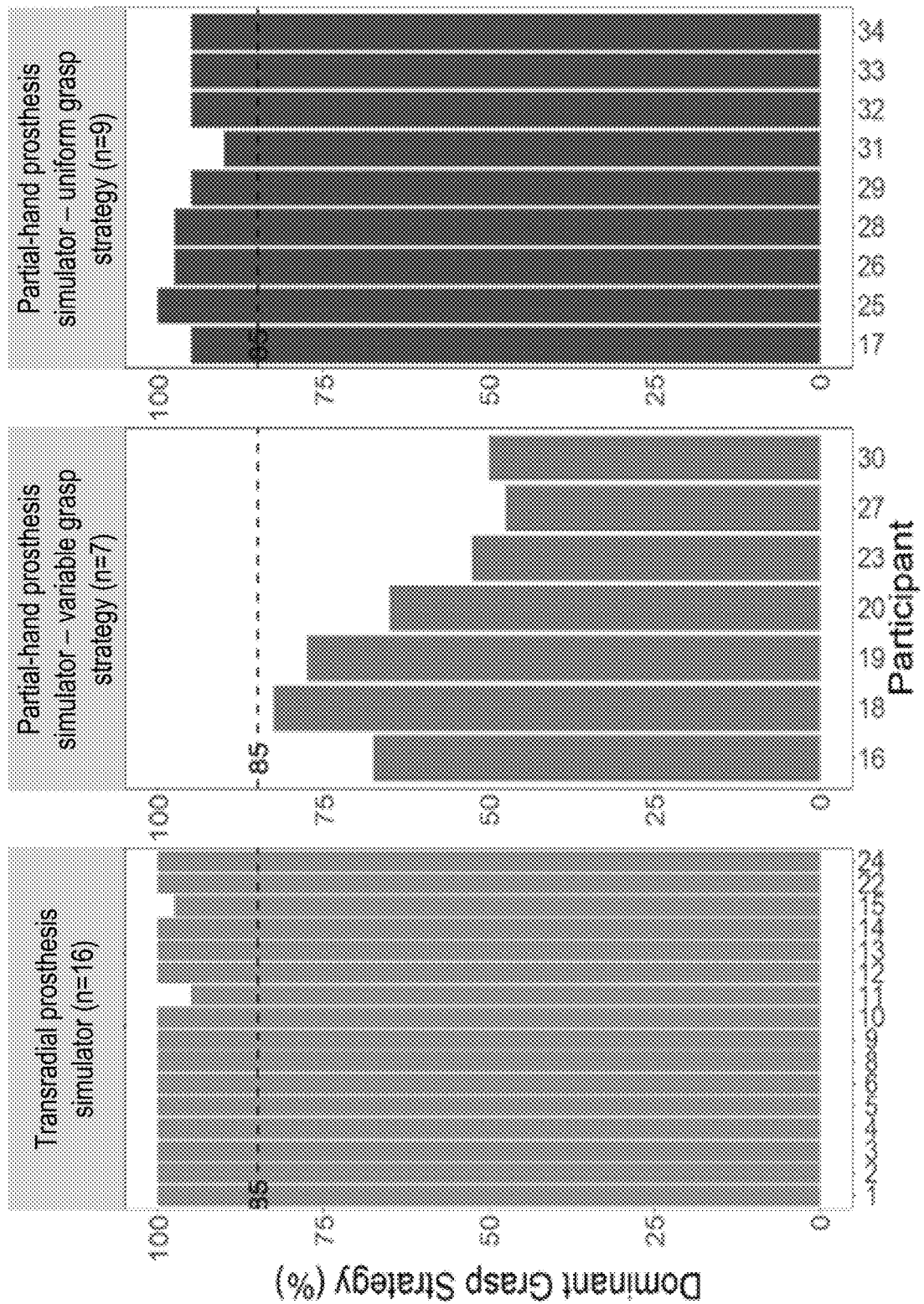
FIG. 4B illustrates a bar graph plotting dominant grasp strategy as a percentage of total grasps for a prosthesis simulator device in accordance with some examples of the present disclosure.

FIG. 4A: Representative plot of grasp strategy with repetition for a single participant in the TrPS, PhPS Variable, and PhPS Uniform groups. FIG. 4B: Bar graph plotting each participant's dominant grasp strategy as a percentage of their total grasps. An 85% threshold (dashed line) demarcates the PhPS Uniform from the PhPS Variable group. 0: grasp from above, 1: grasp from the side, 2: other grasp strategy.

FIG. 5A: Bar graph demonstrating the significant difference between dominant grasp strategy between all three groups in the Rotation task. FIG. 5B: Bar graph demonstrating the lack of difference between grasp strategy in the Translation task. Groups were maintained from the Rotation task. Error bars denote standard error. Significance at p<0.05.

FIG. 6A: Bar graph demonstrating movement duration for the Rotation task. All groups show decreases in duration with repeated trials. PhPS groups are not significantly different from each other or the TrPS group. FIG. 6B: Bar graph demonstrating movement duration for the Translation task. Only PhPS groups show decreases in duration with repeated trials but are not significantly different from each other or the TrPS group. Error bars denote standard error. Significance at p<0.05.

FIG. 7A: Bar graph demonstrating reach peak velocity for the Rotation task. Only the PhPS groups show increases in reach peak velocity with repeated trials. In later trials, the PhPS show significantly higher reach peak velocities than the TrPS group, but do not differ between each other. FIG. 7B: Bar graph demonstrating reach peak velocity for the Translation task. Only the PhPS Uniform group shows a significant increase in reach peak velocity over time. Error bars denote standard error. Significance at p<0.05.

What is claimed is:

1. A prosthesis simulator comprising:
   a first restraint configured to restrain one or more fingers of a wearer of the prosthesis simulator;
   a second restraint configured to restrain a thumb of the wearer; and
   one or more artificial digits configured to move in a manner to simulate one or more prosthetic fingers and a prosthetic thumb of a prosthesis;
   wherein the prosthesis simulator is configured to enable the wearer to open at least one of the artificial digits through wrist flexion and close at least one of the artificial digits through wrist extension.

2. The prosthesis simulator of claim 1 further comprising:
   a cuff on a proximal end of the prosthesis simulator, the cuff configured to detachably attach to an arm of the wearer;
   a base plate hingedly coupled to the cuff thereby allowing the base plate to rotate relative to the cuff; and a rod connecting the artificial digits to the base plate;
wherein an articulation of the base plate relative to the cuff causes an articulation of the artificial digits by the rod.

3. The prosthesis simulator of claim 2, wherein the first restraint is attached to a roof plate connected to the base plate and defining a dorsal side of the prosthesis simulator; and
wherein the second restraint is attached to a holster connected to the base plate on a palmar side of the prosthesis simulator.

4. The prosthesis simulator of claim 3, wherein the first restraint is slidably attached to the roof plate such that the first restraint can be positioned at varying distances away from the base plate.

5. The prosthesis simulator of claim 2 further comprising a joint connecting the base plate to the cuff;
wherein the rod attaches the joint.

6. The prosthesis simulator of claim 1, wherein each of the artificial digits comprises a polymer material and a silicone-based material.

7. The prosthesis simulator of claim 6, wherein the artificial digits are positioned in a 3 jaw chuck grasp.

8. The prosthesis simulator of claim 1 further comprising:
a base plate;
a roof plate connected to the base plate and defining a dorsal side of the prosthesis simulator; and
a holster connected to the base plate on a palmar side of the prosthesis simulator opposite the dorsal side;
wherein:
the one or more artificial digits extend from the base plate on the palmar side of the prosthesis simulator;
the first restraint is configured to restrain the one or more fingers of an unaffected hand of the wearer of the prosthesis simulator to the roof plate;
the second restraint is configured to restrain the thumb of the unaffected hand of the wearer;
the second restraint is attached to the holster; and
the one or more artificial digits are configured to move in a manner to simulate the one or more prosthetic fingers and the prosthetic thumb of the prosthesis worn on an affected hand of the wearer.

9. The prosthesis simulator of claim 8 further comprising:
a cuff on a proximal end of the prosthesis simulator, the cuff configured to detachably attach to the arm with the unaffected hand of the wearer;
a joint connecting the base plate to the cuff; and
a rod connecting the artificial digits to the base plate;
wherein an articulation of the base plate relative to the cuff causes an articulation of the artificial digits by the rod.

10. The prosthesis simulator of claim 9, wherein the prosthesis simulator is further configured to enable the wearer to perform a task with at least one of the artificial digits via the articulation of the base plate relative to the cuff, causing the articulation of the artificial digits by the rod.

11. The prosthesis simulator of claim 8, wherein the prosthesis simulator is configured to preserve the wearer's perception of arm length of the arm with the unaffected hand.

12. The prosthesis simulator of claim 8, wherein the first restraint and the second restraint are further configured to restrain portions of the unaffected hand in an open hand posture.

13. The prosthesis simulator of claim 8, wherein the first restraint is further configured to be slidably attached to the roof plate such that the first restraint can be positioned at varying distances away from the base plate.

14. The prosthesis simulator of claim 8, wherein the one or more artificial digits are configured to form at least a portion of a 3 jaw chuck grasp with the thumb constrained at a right angle secured along the palm of the unaffected hand.

15. A partial-hand prosthesis simulator (PhPS) comprising:
a first restraint configured to restrain one or more fingers of a wearer of the PhPS;
a second restraint configured to restrain a thumb of the wearer; and
one or more artificial digits configured to move in a manner to simulate one or more prosthetic fingers and a prosthetic thumb of a prosthesis;
wherein:
the PhPS is configured to enable the wearer to open at least one of the artificial digits through wrist flexion and close at least one of the artificial digits through wrist extension.

16. An amputation simulator device comprising:
a cuff on a proximal end of the amputation simulator device, the cuff configured to detachably attach to an arm of a wearer of the amputation simulator device;
a roof plate hingedly coupled to the cuff and defining a dorsal side of the amputation simulator device, the roof plate comprising a first restraint configured to restrain one or more fingers of the wearer;
a holster attached to the roof plate on a palmar side of the amputation simulator device opposite the dorsal side, the holster comprising a second restraint configured to restrain a thumb of the wearer;
artificial digits extending from the roof plate on the palmar side of the amputation simulator device, the artificial digits configured to move in a manner to simulate one or more prosthetic fingers and a prosthetic thumb of a prosthesis; and
a rod connecting the artificial digits to the cuff;
wherein the amputation simulator device is configured to enable the wearer to open at least one of the artificial digits through wrist flexion and close at least one of the artificial digits through wrist extension.

17. The amputation simulator device of claim 16, wherein the first restraint and the second restraint are configured to immobilize the one or more fingers and the thumb, respectively.

18. The amputation simulator device of claim 16, wherein the artificial digits are positioned in a 3 jaw chuck grasp.

19. The amputation simulator device of claim 16, wherein the first restraint is slidably attached to the roof plate such that the first restraint can be positioned at varying distances away from the cuff.

20. The amputation simulator device of claim 16, wherein each of the artificial digits comprises a polymer material and a silicone-based material.

* * * * *